United States Patent [19]

Finkelstein et al.

[11] Patent Number: 4,761,415
[45] Date of Patent: Aug. 2, 1988

[54] DOPAMINE-β-HYDROXYLASE INHIBITORS

[75] Inventors: Joseph A. Finkelstein, Philadelphia, Pa.; Lawrence I. Kruse, Haddonfield, N.J.; Thomas B. Leonard, Haverford, Pa.

[73] Assignee: SmithKline Beckman Corporation, Philadelphia, Pa.

[21] Appl. No.: 901,120

[22] Filed: Aug. 28, 1986

[51] Int. Cl.⁴ ............... A61K 31/495; C07D 403/06; C07D 295/10
[52] U.S. Cl. .................. 514/252; 544/366; 544/400
[58] Field of Search ............ 544/366, 400; 514/252

[56] References Cited

U.S. PATENT DOCUMENTS 3,505,334  4/1970  Regnier et al. ............ 544/401
4,120,864 10/1978  Seidel et al. ............. 260/308 R
4,338,453  7/1982  Gall ...................... 544/366
4,532,331  7/1985  Frazee et al. ............. 548/317

OTHER PUBLICATIONS

Chemical Abstract 76:135847w.
Chemical Abstract 88:170043.
Chemical Abstract 67:38283.
Chemical Abstract 94:65563.
Chemical Abstract 84:44070.
Chemical Abstract 73:36594.
Chemical Abstract 89:215405.
Chemical Abstract 74:99310.
Chemical Abstract 74:111161.
Chemical Abstract 75:146214.
Chemical Abstract 76:85027.
Chemical Abstract 79:104394.
Chemical Abstract 70:37729.
Chemical Abstract 74:141644.
Chemical Abstract 75:98505.
Chemical Abstract 79:66362.
Chemical Abstract 80:54530.
Chemical Abstract 87:15379.
Chemical Abstract 94:39517.
Chemical Abstract 97:79871.
Modi, K. F. et al., *J. Indian Chem. Soc.*, vol. LIV, pp. 741-742 (Jul. 1977).
Lin, Y. et al., *J. Heterocyclic Chem.*, 17, 1077 (1980).
Khadse et al, CA 85-192667k, New Piperazine Derivatives as Antibacterial Agents.
Gall, CA 97-182434c, Aminoalkyl-1,2,4-Triazoles.

*Primary Examiner*—Robert Gerstl
*Assistant Examiner*—Cecilia Shen
*Attorney, Agent, or Firm*—Vincent L. Fabiano; Stuart R. Suter; Alan D. Lourie

[57] ABSTRACT

Potent dopamine-β-hydroxylase inhibitors having the Formula

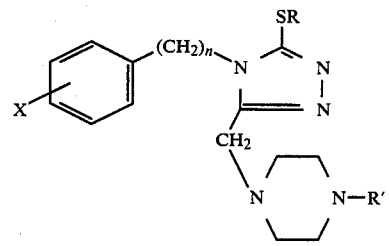

that are useful to inhibit dopamine-β-hydroxylase activity, pharmaceutical compositions including these inhibitors, and methods of using these inhibitors to inhibit dopamine-β-hydroxylase activity in mammals. Also disclosed are novel intermediates useful in preparing the presently invented inhibitors.

15 Claims, No Drawings

DOPAMINE-β-HYDROXYLASE INHIBITORS

FIELD OF THE INVENTION

This invention relates to novel compounds that inhibit dopamine-β-hydroxylase.

BACKGROUND OF THE INVENTION

In the catecholamine biosynthetic pathway, tyrosine is converted in three steps to norepinephrine (NE). Intermediates are dihydroxyphenylalanine (DOPA) and dopamine (DA). Dopamine is hydroxylated to norepinephrine by dopamine-β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels, which as reported by Ehrreich et al., "New Antihypertensive Drugs," *Spectrum Publishing*, 1976, pp. 409–432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159–165 and by Osumi et al., *Japan J. Pharmacol.* 23, 904 (1973).

A number of DBH inhibitors are known. These generally are divided into two classes, namely, metal chelating agents, which bind copper in the enzyme, and phenethylalamine analogues. Rosenberg et al., "Essays in Neurochemistry and Neuropharmacology," Vol. 4, ed. by Youdim et al., John Wiley & Sons, 1980, pp. 179–192, and Goldstein, *Pharmacol. Rev.* 18(1), 77 (1966), review DBH inhibitors. The former report that many potent DBH inhibitors have a hydrophobic side chain of size comparable to the aromatic ring of DA, leading the authors to suggest that incorporation of a terminal hydroxyl group on a 4- to 6- carbon side chain on a phenethylalamine analogue may yield potent inhibitors.

Known DBH inhibitors include:

(a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., Mol. *Pharmacol.* 9, 172 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976)];

(b) BRL 8242 [See Claxton et al., *Eur J. Pharmacol.* 37, 179 (1976)];

(c) 1-alkylimidazole-2-thiols [See, Hanlon et al., *Life Sci.* 12, 417 (1973); Fuller et al., *Adv. Enzyme Regul.* 15, 267 (1976)];

(d) substituted thioureas [See, Johnson et al., *J. Pharmacol. Exp. Ther.* 168, 229 (1969)]; and (e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci* 107, 878 (1963)].

All the above compounds except benzyloxyamine and benzylhydrazine apparently owe their inhibitory effect to metal chelating properties. Alkyl derivatives of imidazole-2-thiol are more potent, presumably due to non-specific interaction of the alkyl substituent with the enzyme. Benzyloxyamine and benzylhydrazine are phenethylalamine analogues which apparently act as competitive inhibitors.

In addition to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5-(4-chlorobutyl) picolinic acid, and others such as substituted amides of fusaric acid and acids and amides of 5-butyroylpicolinic acid, 5-aminopicolinic acid and 5-hydrazinopicolinic acid, and derivatives thereof. Hidaka et al., *Molecular Pharmacology*, 9, 172–177 (1972) report that 5-(3,4-dibromobutyl)picolinic acid and 5-(dimethyldithiocarbamoylmethyl)picolinic acid are DBH inhibitors.

Bupicomide, 5-(n-butyl)picolinamine, is reported by Ehrreich et al., "*New Antihypertensive Drugs*", Spectrum Publications, 1976, pg. 409–432, to be a DBH inhibitor that has antihypertensive activity.

In European Pat. Application No. 125,033 (published Nov. 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of *Streptoverticillium*. These compounds inhibit DBH activity.

U.S. Pat. No. 4,532,331 describes various 1-benzyl-2-aminomethyl imidazole derivatives that inhibit DBH activity and includes pharmaceutical compositions containing these derivatives and methods of using these derivatives to inhibit DBH activity.

Non-specific, often toxic effects to known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structure interacts with a number of metalloproteins and enzymes non-specifically to produce the observed side effects.

4-Aralkyl substituted-1,2,4-triazole-3-thiols having the following structure have been synthesized previously

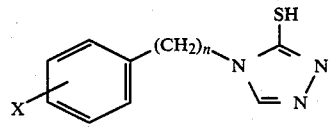

in which:

n is O and X is hydrogen, $CH_3$, $OCH_3$, $OCH_2CH_3$, $OCH_2CH_2CH(CH_3)_2$, Br, Cl, I, $CF_3$, $NO_2$, or COOH, or combinations of the above; and n is 1 and X is hydrogen. See, e.g., Chem. Abstr. 76:135847w; Chem. Abstr. 88:170043; Chem. Abstr. 67:38283; Chem. Abstr. 94:65563; Chem. Abstr. 84:44070; Chem. Abstr. 73:36594; Chem. Abstr. 89:215405.

Certain 1-aralkyl-substituted-1,2,4-triazole-5-thiols also have been prepared previously. These known compounds include compounds having the following formula:

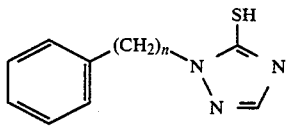

in which n is 0 or 1. See, e.g., Chem. Abstr. 74:99310; Chem. Abstr. 74:111161; Chem. Abstr. 75:146214; Chem. Abstr. 70:37729; Chem. Abstr. 79:66362; Chem. Abstr. 80:54530.

Absent from the above references disclosing the 4-aralkyl-substituted-1,2,4-triazole-3-thiol and 1-aralkyl-substituted-1,2,4-triazole-5-thiol compounds, however, is any suggestion that these compounds possess activity as dopamine-β-hydroxylase inhibitors or are efficacious in the treatment of diseases, such as hypertension, in which reductions in dopamine-β-hydroxylase activity produce therapeutic benefits. These compounds have been employed as reagents in photographic and electrorecording processes and analytical methods. Also, some of these compounds have been used as fungicides, herbicides, and pesticides. Additionally, certain of these compounds were found to inhibit the growth on mice footpads of leprosy-causing bacteria.

SUMMARY OF THE INVENTION

The present invention resides in the discovery that DBH is inhibited by substituted 3-mercapto-4-aralkyl-5-[(4-alkyl-1-piperazinyl)methyl]-1,2,4 and substituted 3-alkylthio-4-aralkyl-5-[(4-alkyl-1piperazinyl)methyl]-1,2,4-triazole compounds. These compounds are potent and produce prolonged DBH inhibition without significantly inhibiting cytochrome $P_{450}$-containing mixed function oxidases.

Presently preferred compounds of the invention and compounds included in the pharmaceutical compositions and used in the methods of the invention include:

3-mercapto-4-benzyl-5-[(4-methyl-1-piperazinyl)methyl]-1,2,4-triazole;

3-mercapto-4-(3-fluorobenzyl)-5-[(4-methyl-1-piperazinyl)methyl]-1,2,4-triazole; and 3-mercapto-4-(3,5-difluorobenzyl)-5-[(4-methyl-1-piperazinyl)methyl]-1,2,4-triazole.

In a further aspect of the invention there are provided novel intermediates useful in preparing substituted 3-mercapto-4-aralkyl-5-[(4-alkyl-1-piperazinyl)methyl]-1,2,4-triazole and substituted 3-alkylthio-4-aralkyl-5-[(4-alkyl-1-piperazinyl)methyl]1,2,4-triazole compounds.

The invention also is a method of inhibiting DBH activity in mammals, including humans, which comprises administering internally to a subject an effective amount of a substituted 3-mercapto-4-aralkyl-5-[(4-alkyl-1-piperazinyl)methyl]-1,2,4-triazole or a substituted 3-alkylthio-4-aralkyl-5-[(4-alkyl-1-piperazinyl)methyl]-1,2,4-triazole compound.

Included in the present invention are pharmaceutical compositions comprising compounds useful in the method of the invention and a pharmaceutical carrier.

DETAILED DESCRIPTION OF THE INVENTION

The presently invented compounds that inhibit DBH have the following formula:

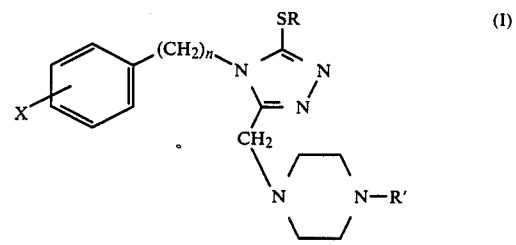

in which: X is H, F, Cl, Br, I, $C_{1-4}$ alkyl, CN, $NO_2$, $SO_2NH_2$, COOH, OH, CHO, $C_{1-4}$ alkoxy, $CH_2OH$, $CF_3$, $SO_2CH_3$, or $CO_2C_aH_{2a+1}$ wherein a is 1–5, or any accessible combination thereof of up to 5 substituents; or n is 0–5;

R and R' independently are hydrogen or $C_{1-4}$ alkyl; and any pharmaceutically acceptable salt or hydrate thereof.

As used herein, "accessible combination thereof" means any other combination of the substituents that is available by chemical synthesis and is stable.

It is intended that Formula I includes the tautomer of the compounds in which R is hydrogen, that is, compounds having the above formula wherein the triazole moiety has either of the below formulae:

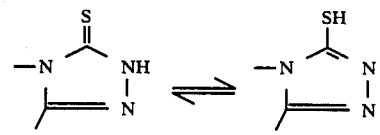

The compounds of Formula I are prepared from N-alkylpiperazines by processes such as shown in Scheme I, below. The starting N-alkylpiperazines are known and described in published references and can be purchased or readily prepared.

In Scheme I, R', X, and n are the same as in Formula I. Scheme I illustrates reaction of N-alkylpiperidines (A) with, preferably methylchloroacetate, but suitably any $C_{1-4}$ alkyl ester of a haloacetic acid, to form 2-(4-alkyl-1-piperazinyl) acetic acid alkyl esters such as 2-(4-methyl-1-piperazinyl) acetic acid methyl ester (B). This reaction is performed in an inert organic solvent such as ethyl ether, tetrahydrofuran, various lower alkyl alcohols, dimethylformamide, or, preferably, ethyl acetate.

Formula (B) compounds then are reacted with hydrazine in a non-ester organic solvent such as various lower alkyl alcohols, ethyl ether, tetrahydrofuran, dimethylformamide, preferably ethanol to yield acylhydrazines (C).

Either of two synthetic routes thereafter can be employed to prepare the 3-mercapto-4-aralkyl-5-[(4-alkyl-1-piperazinyl)methyl]-1,2,4-triazole compounds of the invention. Each of the synthetic alternatives involves reaction of the acylhydrazines (C) with a substituted aralkylisothiocyanate. The substituted aralkylisothiocyanates are selected so that the X and n values correspond to those of the desired formula (E) compound. In one of the synthetic routes the reaction of formula (C) compounds with substituted aralkylisothiocyanates is carried out in an inert organic solvent and produces formula (D) intermediate compounds. Cyclization of formula (D) compounds with an alcoholic base such as a lower alkoxide in the corresponding lower alkanol, for example sodium ethoxide in ethanol, produces formula (E) compounds of the invention. Alternatively, formula (E) compounds are prepared by extended reaction of formula (C) compounds with the substituted isothiocyanates in a lower alkanol, preferably ethanol. This alternate procedure is favored for ease of handling and higher yield.

Compounds of the invention in which R is $C_{1-4}$ alkyl are prepared by alkylating the corresponding formula (E) compound with, for example, methyl iodide in methanol by known procedures. Other alkyl halides such as methyl bromide or methyl chloride, in appropriate solvents, can be substituted for methyl iodide. Further, the compounds in which R is an alkyl group other than methyl are prepared by reacting the corresponding formula (E) compound with an alkyl halide, such as butyl iodide, in an appropriate solvent to yield the desired 3-alkylthio-4-aralkyl-5-[(4-alkyl-1-piperazinyl)methyl]-1,2,4-triazole of the invention.

SCHEME I

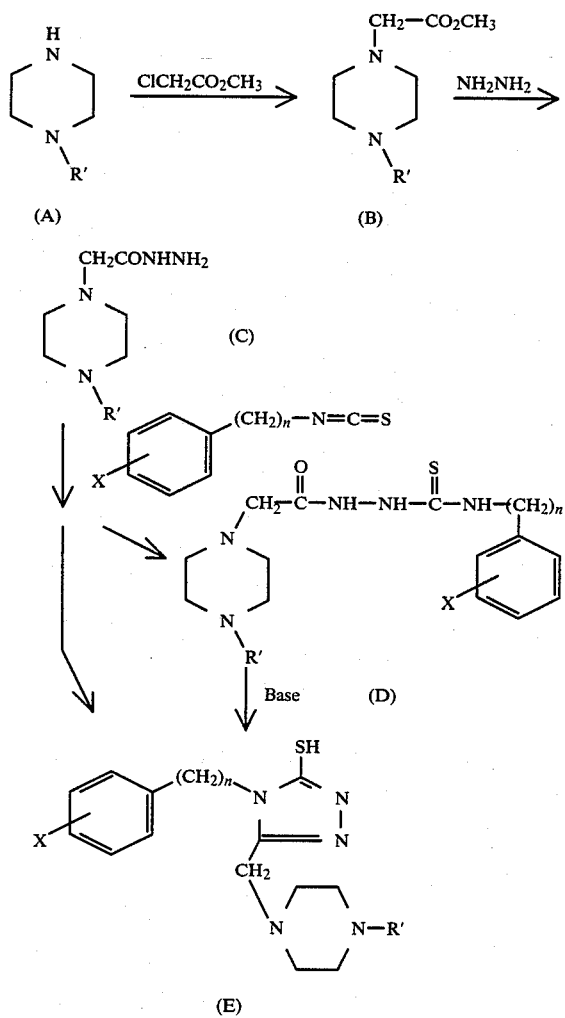

In preparing the presently invented compounds of Formula I, novel intermediate compounds of the following formula were synthesized:

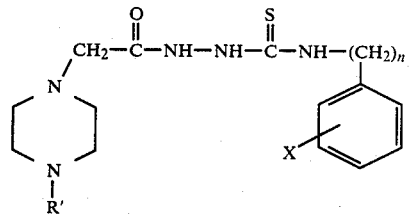

in which

X is H, F, Cl, Br, I, $C_{1-4}$ alkyl, CN, $NO_2$, $SO_2NH_2$, COOH, OH, CHO, $C_{1-4}$ alkoxy, $CH_2OH$, $CF_3$, $SO_2CH_3$, $SO_2CF_3$, or $CO_2C_aH_{2a+1}$ wherein a is 1-5, or any accessible combination thereof of up to 5 substituents; or n is 0-5;

R' is hydrogen or $C_{1-4}$ alkyl.

The pharmaceutically acceptable acid addition salts of compounds of the invention are formed with strong or moderately strong organic or inorganic acids by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate, quinate, and nitrate salts.

Because the Formula I compounds inhibit DBH activity, they have therapeutic value as diuretic, natriuretic, cardiotonic, antihypertensive, and vasodilator agents, as well as antiulcerogenic and anti-Parkinsonian agents. Listed in Table I are the compounds of the invention and a potent reference compound included in application Ser. No. 590,665 that were tested for in vitro DBH inhibition by a standard procedure for assaying conversion of tyramine to octopamine in the presence of DBH. J. J. Pisano, et al., *Biochim. Biophys. Acta*, 43, 566–568 (1960). Octopamine was assayed following sodium periodate oxidation to p-hydroxybenzaldehyde by measuring spectrophotometric absorbance at 330 nm. In Table I, inhibition is given in molar concentration of compound at which DBH activity was halved ($IC_{50}$) Fusaric acid, by this test was found to have an $IC_{50}$ of $8 \times 10^{-7}$ M.

TABLE I

| Compound | DBH $IC_{50}$ | P-450 $IC_{50}$ |
|---|---|---|
| 3-mercapto-4-benzyl-5-[(4-methyl-1-piperazinyl)methyl]-1,2,4-triazole hydrochloride | $9.0 \times 10^{-5}$ M | 700 μM |
| 3-mercapto-4-(3-fluorobenzyl)-5-[(4-methyl-1-piperazinyl)methyl]-1,2,4-triazole | $6.0 \times 10^{-5}$ M | 375 μM |
| 3-mercapto-4-(3,5-difluorobenzyl)-5-[(4-methyl-1-piperazinyl)methyl]-1,2,4-triazole | $5.0 \times 10^{-5}$ M | 350 μM |
| 1-(3,5-difluorobenzyl)-2-mercapto imidazole (Reference Compound) | $1.2 \times 10^{-6}$ M | 12 μM |

The compounds listed in Table I also were evaluated for their ability to inhibit cytochrome P450-dependent mixed function oxidase catalyzed deethylation of ethoxycoumarin by the procedure of Greenlee and Poland, *J. Pharmacol. Exp. Ther.*, 205, 596–605 (1978). When compared to the reference compound, the compounds of the invention also are potent DBH inhibitors but are from approximately 30 to 60-fold less potent as mixed function oxidase inhibitors.

Further, spontaneously hypertensive rats were treated with a suspension or solution of 3-mercapto-4-benzyl-5-[(4-methyl-piperazinyl)methyl]-1,2,4-triazole or 3-mercapto-4-(3-fluorobenzyl)-5[(4-methyl-1-piperazinyl)methyl]-1,2,4-triazole at a dose of 50 mg/kg intraperitoneally, and mean arterial blood pressure was monitored for 260 minutes using indwelling cannulae in the tail arteries. When compared to vehicle-treated controls, the animals treated with each of the compounds exhibited significant blood pressure reductions within 30 minutes following treatment. The maximal blood pressure reductions were approximately 25 and 40 mmHg, respectively, for each of the administered compounds.

The compounds of Formula I can be incorporated into convenient pharmaceutical dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds of Formula I in a pharmaceutical dosage unit as described above will be an efficacious, nontoxic quantity selected from the range of 0.1–100 mg/kg of active compound, preferably 0.1–50 mg/kg. The selected dose is administered to a human patient in need of DBH inhibition from 1–6 times daily, orally, rectally, by injection, or continuously by infusion. Oral dosage units for human administration preferably contain from 1 to 500 mg of active compound. Parenteral administration, which uses lower dosages is preferred. Oral administration, at higher dosages, however, also can be used when safe and convenient for the patient.

The method of this invention of inhibiting DBH activity in mammals, including humans, comprises administering internally to a subject in need of such inhibition an effective DBH inhibiting amount of a compound of Formula I.

The following examples are illustrative of preparation of Formula I compounds. The examples are not intended to limit the scope of the invention as defined hereinabove and as claimed below.

EXAMPLE 1

3-Mercapto-4-benzyl-5-[(4-methyl-1-piperazinyl)methyl]-1,2,4-triazole

Methyl chloroacetate (8.8 ml., 0.10 mole) was added to a solution of N-methylpiperazine (24.4. ml., 0.22 mole) in ethyl acetate (140 ml.) and the mixture was stirred for 17 hours. The reaction mixture was filtered and the solvent was removed under vacuum. The resulting oil was dissolved in methylene chloride-methanol (9:1) and purified by flash chromatography (silica) to give 2-(4-methyl-1-piperazinyl)acetic acid, methyl ester as an oil (16.3 g, 95%).

A solution of 2-(4-methyl-1-piperazinyl)acetic acid, methyl ester (16.3 g., 0.0946 mole) and hydrazine monohydrate (7.0 ml., 0.142 mole) in ethanol (100 ml.) was refluxed for 17 hours and the solvent was removed under vacuum. The residue was triturated with ether with cooling at −78° and the resulting solid was filtered. The product was triturated again with ether-ethyl acetate to give 2-(4-methyl-1-piperazinyl)acetic acid, hydrazide as a solid melting at 87°–89° C. (8.94 g., 55%).

A solution of 2-(4-methyl-1-piperazinyl)acetic acid, hydrazide (2.58 g., 0.015 mole) and benzyl-isothiocyanate (2.0 ml., 0.015 mole) in ethanol (75 ml.) was refluxed for 1 hour. Additional benzylisothiocyanate (1.5 ml.) was added and the solution was refluxed for 15 minutes. The solvent was removed under vacuum and residue was triturated with ether. The resulting solid was filtered and recrystallized from ethanol to give 1-(4-methyl-1-piperazinylacetyl)-4-benzyl-thiosemicarbazide (4.56 g., 95%).

Crude 1-(4-methyl-1-piperazinylacetyl)-4-benzyl-thiosemicarbazide was added to a solution of sodium ethoxide [from sodium (0.90 g., 0.039 mole) in ethanol (100 ml.)]and the solution was refluxed for 17 hours. The mixture was filtered and the solvent was removed under vacuum. The resulting oil was dissolved in water and the solution was acidified to pH 7 with 10% HCl. The crude product was filtered and recrystallized from ethanol to give 3-mercapto-4-benzyl-5-[(4-methyl-1-piperazinyl)methyl]-1,2,4-triazole a solid melting at 223°–225° C. (3.0 g., 76%).

EXAMPLE 2

3-Mercapto-4-(3-fluorobenzyl)-5-[(4-methyl-1-piperazinyl)methyl]-1,2,4-triazole

A solution of 3-fluorobenzylamine (6.26 g., 0.05 mole) in ether (10 ml.) was added dropwise to a solution of dicyclohexylcarbodiimide (10.3 g., 0.05 mole) and carbon disulfide (20 ml., 0.333 mole) in ether (60 ml.) at −5° to −10° C. and the mixture was stirred for 17 hours at 25° C. The mixture was filtered, and the solvent was removed under vacuum. The resulting oil was dissolved in hexane-ethyl acetate (19:1), filtered and the solvent removed under vacuum. The oil was then dissolved in hexane-ethyl acetate (9:1) and purified by flash chromatography (silica) to give 3-fluorobenzylisothiocyanate as an oil (8.14 g., 97%).

A solution of 2-(4-methyl-1-piperazinyl)acetic acid, hydrazide (2.58 g., 0.015 mole) and 3-fluorobenzylisothiocyanate (2.51 g., 0.015 mole) in ethanol (30 ml.) was refluxed for 17 hours and the solvent was removed under vacuum. The residue was triturated with ether and the resulting solid was filtered and recrystallized from ethyl acetate to give 3-mercapto-4-(3-fluorobenzyl)-5-[(4-methyl-1-piperazinyl)methyl]-1,2,4-triazole as a solid melting at 179.5°-180.5° C. (2.30 g., 48%).

EXAMPLE 3

3-Mercapto-4-(3,5-difluorobenzyl)-5-[(4-methyl-1-piperazinyl)methyl]-1,2,4-triazole A mixture of 3,5-difluorobenzonitrile (13.9 g., 0.10 mole) in methanol [(140 ml.), saturated with ammonia-]and Raney nickel was shaken under hydrogen (50 psi.) for 1.5 hours and the solution was decanted from the catalyst. The solution was filtered, evaporated to an oil, and dissolved in ethyl acetate. The ethyl acetate solution was extracted twice with 1N HCl (75 ml.) and the aqueous solution was washed once with ethyl acetate, made basic with 10% sodium hydroxide, and extracted with three portions of ethyl acetate (100 ml.). The ethyl acetate solution was washed with water and brine, dried, and the solvent removed under vacuum. The residue was diluted with ether, filtered, and the solvent was removed under vacuum to give 3,5-difluorobenzylamine as an oil (11.7 g., 82%).

A solution of 3,5-difluorobenzylamine (11.6 g., 0.081 mole) in ether (20 ml.) was added dropwise to a solution of dicyclohexylcarbodiimide (16.7 g., 0.081 mole) and carbon disulfide (32.4 ml., 0.539 mole) in ether (100 ml.) at −5° to −10° C., and the mixture was stirred for 17 hours at 25° C. The mixture was filtered and the solvent was removed under vacuum. The resulting oil was dissolved in hexane-ether (19:1), filtered, and the solvent removed under vacuum. The oil was then dissolved in hexane and purified by flash chromatography (silica) to give 3,5-difluorobenzylisothiocyanate as an oil (5.40 g., 36%).

A solution of 2-(4-methyl-1-piperazinyl)acetic acid, hydrazide (3.44 g., 0.020 mole) and 3,5-difluorobenzylisothiocyanate (3.70 g., 0.020 mole) in ethanol (40 ml.) was refluxed for 17 hours and the solvent was removed under vacuum. The residue was triturated with ethyl acetate-ether and the resulting solid was filtered and recrystallized twice from ethanol to give 3-mercapto-4-(3,5-difluorobenzyl)-5-[(4-methyl-1-piperazinyl)methyl]-1,2,4-triazole as a solid melting at 200°-201° C. (4.60 g., 68%).

EXAMPLE 4

3-Methylthio-4-benzyl-5-[(4-methyl-1-piperazinyl)methyl]-1,2,4-triazole

The reaction of 3-mercapto-4-benzyl-5-[(4-methyl-piperazinyl)methyl]-1,2,4-triazole prepared as in Example 1 with methyl iodide and sodium methoxide in methanol by standard techniques yields 3-methylthio-4-benzyl-5-[(4-methyl-1-piperazinyl)methyl]-1,2,4-triazole.

EXAMPLE 5

3-Mercapto-4-(3-phenylpropyl)-5-[(4-methyl-1-piperazinyl)methyl]-1,2,4-triazole

The process of Example 1 wherein benzylisothiocyanate is replaced by 3-phenylpropylisothiocyanate yields 3-mercapto-4-(3-phenylpropyl)-5-[(4-methyl-1-piperazinyl)methyl]-1,2,4-triazole.

EXAMPLE 6

3-Mercapto-4-(3-methoxybenzyl)-5-[(4-methyl-1-piperazinyl)methyl]-1,2,4-triazole The process of Example 1 wherein benzylisothiocyanate is replaced by 3-methoxybenzylisothiocyanate yields 3-mercapto-4-(3-methoxybenzyl)-5-[(4-methyl-1-piperazinyl)methyl]-1,2,4-triazole.

EXAMPLE 7

3-Mercapto-4-(3-hydroxybenzyl)-5-[(4-methyl-1-piperazinyl)methyl]-1,2,4-triazole Reaction according to standard procedures of boron tribromide (40% BBr$_3$ in methylene chloride) with 3-mercapto-4-(3-methoxybenzyl)-5-[(4-methyl-1-piperazinyl)methyl]-1,2,4-triazole in methylene chloride yields 3-mercapto-4-(3-hydroxybenzyl)-5-[(4-methyl-1-piperazinyl)methyl]-1,2,4-triazole.

EXAMPLE 8

3-Mercapto-4-benzyl-5-[(4-propyl-1-piperazinyl)methyl]-1,2,4-triazole

The process of Example 1 wherein N-methylpiperazine is replaced by N-propylpiperazine yields 3-mercapto-4-benzyl-5-[(4-propyl-1-piperazinyl)methy]-1,2,4-triazole.

EXAMPLE 9

The process of Example 1 wherein benzylisothiocyanate is replaced by 3-bromobenzylisothiocyanate yields 3-mercapto-4-(3-bromobenzyl)-5-[(4-methyl-1-piperazinyl)methyl]-1,2,4-triazole.

EXAMPLE 10

The process of Example 1 wherein benzylisothiocyanate is replaced by 3-ethylbenzylisothiocyanate yields 3-mercapto-4-(3-ethylbenzyl)-5-[(4-methyl-1-piperazinyl)methyl]-1,2,4-triazole.

EXAMPLE 11

The process of Example 1 wherein benzylisothiocyanate is replaced by 3-cyanobenzylisothiocyanate yields 3-mercapto-4-(3-cyanobenzyl)-5-[(4-methyl-1-piperazinyl)methyl]-1,2,4-triazole.

EXAMPLE 12

The process of Example 1 wherein benzylisothiocyanate is replaced by 3-acetoxybenzylisothiocyanate yields 3-mercapto-4-(3-acetoxybenzyl)5-[4-methyl-1-piperazinyl)methyl]-1,2,4-triazole.

EXAMPLE 13

The process of Example 1 wherein benzylisothiocyanate is replaced by 3-trifluoromethylbenzylisothiocyanate yields 3-mercapto-4-(3-trifluoromethylbenzyl) -5-[(4-methyl-1-piperazinyl)methyl]-1,2,4-tr

EXAMPLE 14

The process of Example 1 wherein benzylisothiocyanate is replaced by 4-nitrobenzylisothiocyanate yields 3-mercapto-4-(4-nitrobenzyl)-5-[(4-methyl-1piperazinyl)methyl]-1,2,4-triazole.

EXAMPLE 15

The process of Example 1 wherein benzylisothiocyanate is replaced by 4-hydroxymethylbenzylisothiocyanate yields 3-mercapto-4-(4-hydroxymethylbenzyl) -5-[(4-methyl-1-piperazinyl)methyl]1,2,4-triazole.

EXAMPLE 16

An oral dosage form for administering the presently invented compounds is produced by screening, mixing, and filling into hard gelatin capsules the ingredients in the proportions shown in Table III, below.

TABLE III

| Ingredients | Amounts |
|---|---|
| 3-Mercapto-4-benzyl-5-[(4-methyl-1-piperazinyl)methyl]-1,2,4-triazole | 50 mg |
| magnesium stearate | 5 mg |
| lactose | 75 mg |

EXAMPLE 17

The sucrose, calcium sulfate dihydrate, and Formula I compound shown in Table IV below, are mixed and granulated in the proportions shown with a 10% gelatin solution. The wet granules are screened, dried, mixed with the starch, talc and stearic acid, screened and compressed into a tablet.

TABLE IV

| Ingredients | Amounts |
|---|---|
| 3-Mercapto-4-(3-fluorobenzyl)-5-[(4-methyl-1-piperazinyl)methyl]-1,2,4-triazole | 100 mg |
| calcium sulfate dihydrate | 150 mg |
| sucrose | 20 mg |
| starch | 10 mg |
| talc | 5 mg |
| stearic acid | 3 mg |

EXAMPLE 18

3-Mercapto-4-(3,5-difluorobenzyl)-5-(4-methyl-1-piperazinyl)methyl]-1,2,4-triazole hydrochloride, 75 mg, is dispersed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the formula:

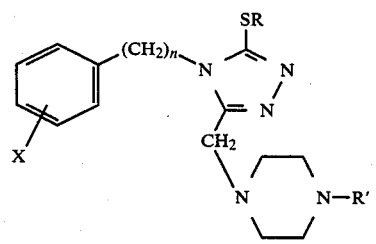

in which:
X is H, F, Cl, Br, I, $C_{1-4}$ alkyl, CN, $NO_2$, $SO_2NH_2$, COOH, OH, CHO, $C_{1-4}$ alkoxy, $CH_2OH$, $CF_3$, $SO_2CH_3$, $SO_2CF_3$, or $CO_2C_aH_{2a+1}$ wherein a is 1-5, or any accessible combination thereof of up to 4 substituents, R and R' independently are H or $C_{1-4}$ alkyl, and
n is 0-5.
a pharmaceutically acceptable salt or hydrate thereof.

2. A compound of claim 1 wherein n is 1.
3. A compound of claim 2 wherein R is H.
4. The compound of claim 3 that is 3-mercapto-4-benzyl-5-[(4-methyl-1-piperazinyl)methyl]-1,2,4-triazole.
5. The compound of claim 3 that is 3-mercapto-4-(3-fluorobenzyl)-5-[(4-methyl-1-piperazinyl)methyl]-1,2,4-triazole.
6. The compound of claim 3 that is 3-mercapto-4-(3,5-difluorobenzyl)-5-[(4-methyl-1-piperazinyl)-methyl]-1,2,4-triazole.
7. A pharmaceutical composition in a dosage unit form for inhibiting dopamine-β-hydroxylase activity comprising a pharmaceutical carrier and an effective amount of a compound of claim 1.
8. A composition of claim 7 in which the compound is 3-mercapto-4-benzyl-5-[(4-methyl-1-piperazinyl)methyl]-1,2,4-triazole.
9. A composition of claim 7 in which the compound is 3-mercapto-4-(3-fluorobenzyl)-5-[(4-methyl-1-piperazinyl)methyl]-1,2,4-triazole.
10. A composition of claim 7 in which the compound is 3-mercapto-4-(3,5-difluorobenzyl)-5-[(4-methyl-1-piperazinyl)methyl]-1,2,4-triazole.
11. A method of inhibiting dopamine-β-hydroxylase activity in mammals that comprises administering internally to a subject in need of such inhibition an effective amount of a compound of claim 1.
12. The method of claim 11 in which the compound is 3-mercapto-4-benzyl-5-[(4-methyl-1-piperazinyl)methyl]-1,2,4-triazole.
13. The method of claim 11 in which the compound is 3-mercapto-4-(3-fluorobenzyl)-5-[(4-methyl-1-piperazinyl)methyl]-1,2,4-triazole.
14. The method of claim 11 in which the compound is 3-mercapto-4-(3,5-difluorobenzyl)-5-[(4-methyl-1-piperazinyl)methyl]-1,2,4-triazole.
15. A compound represented by the formula:

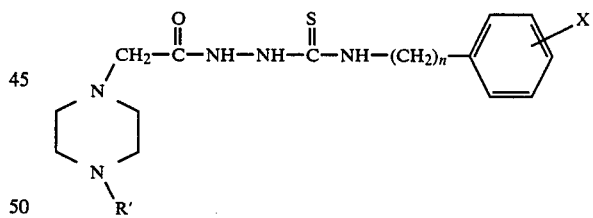

in which:
X is H, F, Cl, Br, $C_{1-4}$ alkyl, CN, $NO_2$, $SO_2NH_2$, COOH, OH, CHO, $C_{1-4}$ alkoxy, $CH_2OH$, $CF_3$, $SO_2CH_3$, $SO_2CF_3$, or $CO_2C_aH_{2a+1}$ wherein a is 1-5, or any accessible combination thereof of up to 4 substituents, R' is H or $C_{1-4}$ alkyl, and
n is 0-5.

* * * * *